United States Patent [19]

Herrin et al.

[11] 4,456,593

[45] Jun. 26, 1984

[54] RISTOCETIN ψ-AGLYCONE AS AN ANTIBACTERIAL AGENT

[75] Inventors: Thomas R. Herrin, Waukegan; Alford M. Thomas, Wadsworth, both of Ill.

[73] Assignee: Abbott Laboratories, North Chicago, Ill.

[21] Appl. No.: 391,079

[22] Filed: Jun. 22, 1982

[51] Int. Cl.³ .................... A61K 37/00; C07C 103/52
[52] U.S. Cl. ............................ 424/177; 260/112.5 R
[58] Field of Search ................. 260/112.5 R; 424/177

[56] References Cited

U.S. PATENT DOCUMENTS 4,322,343  3/1982  Debono ................... 260/112.5 R

OTHER PUBLICATIONS

J. R. Kalman, et al., Journal of the American Chemical Society 102, (1980) 897–905.

*Primary Examiner*—Delbert R. Phillips
*Attorney, Agent, or Firm*—Martin L. Katz; Steven F. Weinstock

[57] ABSTRACT

Described is the use of ψ-aglycone and other derivatives of ristocetin A as antibacterial agents.

6 Claims, No Drawings

RISTOCETIN ψ-AGLYCONE AS AN ANTIBACTERIAL AGENT

BACKGROUND OF THE INVENTION

The antibiotic ristocetin A, described in U.S. Pat. No. 2,990,329 issued June 27, 1961, has been used in the treatment of infections caused by staphylococcus organisms and resistant to penicillin. The antibiotic vancomycin, described in U.S. Pat. No. 3,067,099 issued Dec. 4, 1962 is now used for the same purpose. Ristocetin has a favorable mode of action in that it is believed it interferes with synthesis of the bacterial wall by preventing the bacterial enzymes from acting on the substrate. Due to this mode of action, no bacterial resistance to ristocetin has developed. Ristocetin, however, is difficult to manufacture and has exhibited some toxicity.

Gram-negative micro-organisms are difficult to treat. It is known that they exclude the penetration of large molecules such as erythromycin antibiotic. It would therefore be desirable to develop an antibiotic which would retain the mechanism of action of ristocetin and at the same time be of smaller molecular weight and hence effective against gram-negative micro-organisms.

SUMMARY OF THE INVENTION

While the structure of ψ-aglycone of ristocetin is known (J. Am. Chem. Soc., 1980, 102, 897), its use as an antibacterial agent has not been described. This invention relates to the use of ψ-aglycone and other derivatives of ristocetin A as antibacterial agents which have been found to be 5–6 times more active than ristocetin A against gram-positive bacteria.

DETAILED DESCRIPTION OF THE INVENTION

The compounds of this invention are represented by the following formula

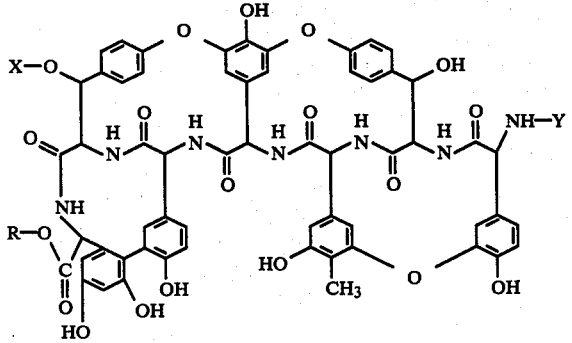

wherein R is hydrogen or loweralkyl, X is hydrogen or ristosamine, Y is hydrogen or acyl, and pharmaceutically acceptable salts thereof.

Ristosamine is represented by the formula

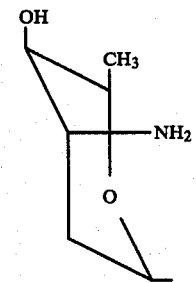

The term "loweralkyl" refers to straight or branched chain alkyl radicals having from 1 to 6 carbon atoms, i.e., methyl, ethyl, n-propyl, iso-propyl, n-butyl, sec-butyl, tert-butyl, n-pentyl, 2-methylbutyl, n-hexyl, 2-methylpentyl, 3-methylpentyl, 2,2-dimethylbutyl and the like.

The term "acyl" as used herein refers to acyl radicals of loweralkyl carboxylic acids represented by the formula

wherein Z is loweralkyl.

The term "pharmaceutically acceptable salts "refers to the nontoxic acid addition salts of compounds of this invention which can be prepared either in situ during the final isolation and purification or by separately reacting the free base with a suitable organic or inorganic acid by methods well known in the art. Representative salts include the mono and di- per salts, such as the sulfate, hydrochloride phosphate, lactate, digluconate, lactobionate, citrate, succinate, tartrate, and the like salts.

The term "sensitive or susceptible strains" refers to strains of bacilli or organisms which have been demonstrated to be sensitive to a particular antibiotic in a standard in vitro sensitivity test and thus in vitro activity has been established for a particular antibiotic against a specific strain of a specific organism.

The compounds of this invention are administered parenterally, i.e., intravenously, intramuscularly, intraperitoneally or subcutaneously for systemic effect in daily dosages of from 20 to 80 mg./kg. daily, preferably from about 25 to about 60, and most preferably from about 25 to 30 mg./kg. of body weight daily, based on lean body weight as is good medical practice with the aminoglycoside antibiotics. It is preferred to administer the compounds of this invention in divided dosages, i.e., three to four times daily. The compounds can also be administered orally at the above dosages to sterilize the intestinal tract and can be further administered in suppository form.

Preparations according to the present invention for parenteral administration include sterile aqueous or nonaqueous solutions, suspensions or emulsions. Examples of nonaqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions and the like.

They can also be manufactured in the form of sterile solid compositions which can be dissolved in sterile water or some other sterile injection medium immediately before use.

Solid dosage forms for oral administration include capsules, tablets, pills, powders and granules. In such solid dosage forms, the active compound is admixed with at least one inert diluent such as sucrose, lactose or starch. Such dosage forms can also comprise, as is normal practice, additional substances other than inert diluents, i.e., lubricating agents such as magnesium stearate. In the case of capsules, tablets and pills, the dosage forms may also comprise buffering agents. Tablets and pills can additionally be prepared with enteric coatings.

Liquid dosage forms for oral administration also include pharmaceutically acceptable emulsions, solutions, suspensions, syrups and elixirs containing inert diluents commonly used in the art, such as water. Besides the inert diluents, the compositions of this invention can also include adjuvants such as wetting agents, emulsifying agents and suspending agents, as well as sweetening and perfuming agents.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment.

In order to illustrate the manner in which the above compounds can be prepared and the properties of the compounds, reference is made to the following examples.

The preparation of the ψ-aglycone of ristocetin was done by methanolysis of ristocetin sulfate in the presence of hydrochloric acid. This compound has been previously reported and the portion and carbon magnetic resonance spectra described. The reaction of ristocetin under more severe hydrolysis conditions led to cleavage of the aminosugar (ristosamine) and hydrolysis of the methyl ester to give O-demethyl ristocetin aglycone. The aglycone was prepared by the reaction of ristocetin ψ-aglycone with triethylsilane in trifluoroacetic acid. These relatively mild conditions gave the aglycone with few impurities. The structure of the ψ-aglycone was determined by comparison of the cmr with the published spectra. The agreement was good with minor differences, possibly due to experiment variables, e.g., temperature, concentration and pH. The cmr of the two aglycones clearly showed the ristosamine moiety was missing as indicated by the absence of the $C_1$, $C_2$, $C_3$ and $C_6$ resonances. The O-demethylaglycone cmr spectrum showed that in addition to lacking the ristosamine, the methyl ester had been cleaved to give the acid of the aglycone. Further spectral data is given in Table I and II.

EXAMPLE 1

Ristocetin ψ-aglycone

Ristocetin A sulfate, 24 g., was dissolved in 640 ml. of 5% hydrochloric acid in methanol and refluxed for 1.25 hours. The solvent was evaporated and the residue treated with ice and the pH adjusted to 6.5 with 0.5N sodium hydroxide. Sufficient ethanol was added to give a homogenous solution and the solution concentrated to about 100 ml. The mixture was filtered to give a light tan powder. An analytical sample was prepared by high pressure liquid chromatography on reverse phase silica (27% dimethylformamide-0.1% phosphoric acid). The 13C nmr spectrum was in agreement with the published spectrum. (M. P. Williamson and D. H. Williams, J. C. S. Perkin I, 1483 (1981). U.V. ($CH_3OH$) max 278 (E max 8,900), $[\alpha]_D -18.77°$ (c 1.06 DMF). The compounds were dissolved in $CD_3SOCD_3$ and the nmr spectra recorded at 70° with a concentration of $0.033 \times 10^{-3}$M. The chemical shifts are ppm from tetramethylsilane.

EXAMPLE 2

O-Demethyl Ristocetin Aglycone

Ristocetin sulfate, 3.00 g., was refluxed in 60 ml. of N hydrochloric acid for 40 minutes. The mixture was cooled to room temperature, adjusted to pH 6.5 with 0.5N sodium hydroxide. The mixture was concentrated at reduced pressure and filtered to give a precipitate, 1.38 g. This material was chromatographed on a 3.0×54 cm. silica gel column and eluted with 1-butanol-/ethyl acetate/water/acetic acid 4/3/2/1. The appropriate fractions were combined and the solvent evaporated to give 0.500 g. of partially purified material. This material was rechromatographed on a second silica gel column to give 250 mg. of product. This material was chromatographed on a 2.4×31 cm $C_{18}$ silica column and eluted with 20% MeOH-0.1% $H_3PO_4$ (adjusted to pH 3 with $Et_3N$). The appropriate tubes were combined and adjusted to pH 6.5 with 0.5N sodium hydroxide and the solution concentrated to remove the methanol. The precipitate was collected to give 115 mg. of product. UV($CH_3OH$) max 278 nm (E 8,600). $[\alpha]_D = 66.7°$ (C 1.08 DMF).

EXAMPLE 3

Ristocetin Aglycone

To a mixture of 1.555 g. (0.0133 mole) of triethylsilane in 25 ml. of trifluoracetic acid was added 1.30 g. (1.00 mmole) of ristocetin-aglycone. The mixture was warmed in a 60°-65° oil bath for 5.5 hours. The solvent was evaporated at reduced pressure. The residue was treated with ice and the pH adjusted to 6.5 with 0.5N sodium hydroxide and the mixture filtered. The precipitate was chromatographed on a 3.0×60 cm silica gel column and the product eluted with 1-butanol/ethyl acetate/water/acetic acid, 4/3/2/1, to give 460 mg. of product. A cmr sample was prepared by chromatography of the purified material on a 2.4×27 cm $C_{18}$ silica column and the column eluted wit 25% methanol-0.1% phosphoric acid (adjusted to pH 3.0 with triethylamine). The appropriate fractions were combined, adjusted to pH 6.5 with 0.5N sodium hydroxide, and concentrated to a small volume. The mixture was filtered to give a white precipitate, 230 mg. UV (methanol) max 278 nm (E 9,100). $[\alpha]_D$ 85° (C. 1.01, dimethylformamide).

TABLE I

| CMR of Ristocetin Aglycone | |
|---|---|
| Chemical Shift, ppm | Assignment |
| 173.9–167.9 | C=O |
| 157.2–102.8 | aromatic |
| 71.7 and 71.4 | Ar—CH(OH)CH(NH—)CO— |
| 62.0–53.3 | Ar CH—NH— |
| 51.6 | $CH_3O$— |
| 8.1 | $ArCH_3$ |

TABLE II

| CMR of O—Demethyl Ristocetin Aglycone | |
|---|---|
| Chemical Shift, ppm | Assignment |
| 173.2–167.2 | C=O |
| 156.7–102.3 | aromatic |
| 71 | Ar CH(OH)CH(NH—)CO— |
| 62.0–53.5 | Ar CH—NH— |
| 8.2 | Ar—CH$_3$ |

EXAMPLE 4

Anti-infective Test-Cure of Acute Mouse Bacterial Infection

Aim:

To determine the ability of potential anti-microbial agents to cure mice of an otherwise lethal infection.

Bacteria:

Bacterial strains used in this test have been previously tested and, if necessary, adapted to mice and are maintained on brain heart infusion (BHI) agar slants at 4° C. Tubes of BHI broth are inoculated from the slants and incubated for 18 hours at 37° C. Serial ten-fold dilutions of this culture are made in BHI broth. The bacterial suspensions used to infect mice are obtained by making the final ten-fold dilution in 5 percent aqueous hog gastric mucin (American Laboratories Incorporated). Mice are infected by an intraperitoneal injection of 0.75 ml. of the resulting suspension. The dilution of test organism selected (standard inoculum) is based on prior experience with that organism and is usually 10–100-fold more concentrated than the LD$_{50}$ dilution, i.e., that concentration which when administered as described above causes 50 percent mortalities.

Test Substances:

The antimicrobial test substance is dissolved at the desired concentration in a suitable vehicle (sterile water, unless otherwise specified) and four serial, two-fold dilutions of this solution are made with the vehicle.

In dosing the animals, all mice are considered to weigh 20 grams. The volume administered is always 0.5 ml. at 1 and 5 hours post-infection (total of 1.0 ml.), with half of the total dose given at each time.

Administration of Test Substances:

The test substance may be administered by any of the following routes:

1. Orally by gavage,
2. Subcutaneously, at the nape of the neck,
3. Intramuscularly in the thigh,
4. Intravenously in the tail vein.

Animals:

Female Swiss albino mice weighing 18 to 20 grams are divided randomly into groups of ten animals and housed one group to a cage. Food (standard mouse pellets) and water are supplied ad lib throughout the test. All animals are sacrificed at the conclusion of the test.

Test:

Group T$_0$ is neither infected nor treated, but is observed for seven days. If more than one mortality occurs in this group, the data will be reviewed to determine is there is cause to invalidate the test.

Groups T$_1$ through T$_4$ are used to monitor the strength of the infection actually used in this experiment. These groups are infected but untreated. Group T$_1$ is infected with the standard inoculum, and groups T$_2$ through T$_4$ are infected with successive ten-fold dilutions of the organism prepared such that only the final dilution in each case is made with 5 percent aqueous hog gastric mucin. These groups are observed for seven days, mortalities are recorded and used to determine the number of challenge LD$_{50}$'s (within ten-fold limits) present in the standard inoculum used to infect medicated groups of animals.

Groups T$_5$ through T$_9$ are infected intraperitoneally with the standard inoculum. Each group is treated with one of the two-fold dilutions of the test substance by a specified route of administration at 1 hour and 5 hours post infection. The animals are observed for seven days and mortalities are recorded.

Further sets of five groups of animals are infected and treated in the same manner as groups T$_5$ through T$_9$ for each additional test substance studied.

CD$_{50}$'s (the total dose, in mg./kg., required to cure half the animals) are calculated by standard statistical methods and are reported with 95 percent confidence limits where these are obtainable or annotated with PS (poor slope) where they are not.

This test is performed in primary and secondary variations. The primary test is run as described above with ten mice in each group. The secondary variation of this test is run with 30 mice in each of groups T$_5$ through T$_9$, and the 95 percent confidence limits to the CD$_{50}$ will, in general, be narrower.

| Compound | Organism | Route Rx | MOUSE PROTECTION Percent Surviving Mice With Varying Drug Dose (mg./kg.) | | | | | | CD$_{50}$* (mg./kg.) |
|---|---|---|---|---|---|---|---|---|---|
| 2 | S. aureus (S) | I.V. | 12.5/100 | 6.25/100 | 3.12/100 | 1.56/60 | — | — mg/kg % | 1.3 (0.01–1.9) |
| 1 | S. aureus (S) | I.V. | 25.0/90 | 12.5/90 | 6.30/50 | 3.10/50 | 1.50/20 | — mg/kg % | 4.1 |
| 2 | S. aureus (S) | I.V. 90 | 25/100 | 12.5/90 | 6.25/50 | 3.12/0 | 1.56 | — mg/kg % | 3.6 (PS)** |
| 1 | S. aureus (S) | I.V. | 50/100 | 25/90 | 12.5/90 | 6.3/50 | 3.1/10 | — mg/kg % | 6.6 |
| 2 | E. coli (J) | I.V. | 50/0 | 25/0 | 12.5/0 | 6.25/0 | 3.12/20 | — mg/kg % | 50 |
| 1 | E. coli (J) | I.V. | 50/0 | 25/20 | 12.5/10 | 6.25/0 | 3.10/0 | — mg/kg % | 50 |

-continued

| | | | MOUSE PROTECTION | | | | | | | |
|---|---|---|---|---|---|---|---|---|---|---|
| Compound | Organism | Route Rx | Percent Surviving Mice With Varying Drug Dose (mg./kg.) | | | | | | | CD$_{50}$* (mg./kg.) |
| 3 | S. aureus (S) | I.V. | 25/80 | 12.5/70 | 6.25/20 | 3.12/20 | 1.56/10 | — | mg/kg % | 9.3 (5.9–17.3) |
| 1 | S. aureus (S) | I.V. | 50/100 | 25/100 | 12.5/90 | 6.3/80 | 3.1/0 | — | mg/kg % | 5.6 (4.2–7.5) |
| 4 | S. aureus (S) | I.V. | 25/100 | 12.5/100 | 6.25/80 | 3.12/0 | —/10 | — | mg/kg % | 4.7 (3.5–6.2) |
| 1 | S. aureus (S) | I.V. | 25/100 | 12.5/90 | 6.25/70 | 3.12/0 | 1.50/0 | — | mg/kg % | ** |
| 4 | S. aureus (S) | S.C. | 50/100 | 25/90 | 12.5/100 | 6.25/90 | 3.12/50 | 1.56/30 | mg/kg % | 2.5 (1.4–3.6) |
| 1 | S. aureus (S) | S.C. | 25/100 | 12.5/90 | 6.25/70 | 3.12/0 | 1.56/10 | — | mg/kg % | 3.7 (2.4–5.7) |
| 2 | S. aureus (SC) | | 25/100 | 12.5/100 | 6.25/80 | 3.12/40 | 1.5/30 | 0.8/0 | 0.4/10 mg/kg % | 2.7 (1.8–4.1) |
| 5 | S. aureus (SC) | | 10/100 | 5/90 | 2.5/80 | 1.2/50 | 0.6/30 | 0.3/10 | 0.15/0 mg./kg. % | 1.1 (0.7–1.8) |
| 6 | S. aureus (SC) | | 10/100 | 5/80 | 2.5/80 | 1.2/60 | 0.6/0 | 0.3/10 | 0.15/10 mg./kg. % | 2.0 (P.S.) |
| 7 | S. aureus (SC) | | 10/100 | 5/40 | 2.5/30 | 1.2/10 | 0.6/10 | 0.3/0 | 0.15/10 mg./kg. % | 3.3 (P.S.) |
| 8 | S. aureus (SC) | | 10/90 | 5/70 | 2.5/60 | 1.2/10 | 0.6/10 | 0.3/10 | mg./kg. % | 2.1 (1.3–3.8) |
| 9 | S. aureus (SC) | | 10/100 | 5/70 | 2.5/60 | 1.2/10 | 0.6/30 | 0.3/20 | mg./kg. % | 1.8 (1.0–3.3) |
| 10 | S. aureus (SC) | | 10/90 | 5/70 | 2.5/70 | 1.2/20 | 0.6/50 | 0.3/40 | mg./kg. % | 1.0 (0.1–2.6) |

1 = Ristocetin
2 = Ristocetin -aglycone
3 = O—demethyl-ristocetin aglycone
4 = Sulfate salt of 3
5 = Phosphate salt of 2
6 = Sulfate salt of 2
7 = Hydrochloride salt of 2
8 = Lactate salt of 2
9 = Diglaconate salt of 2
10 = Lactobionate salt of 2
*Curative dose$_{50}$ using the Probit Statistical Analysis
**Poor slope

What is claimed is:

1. A compound of the formula

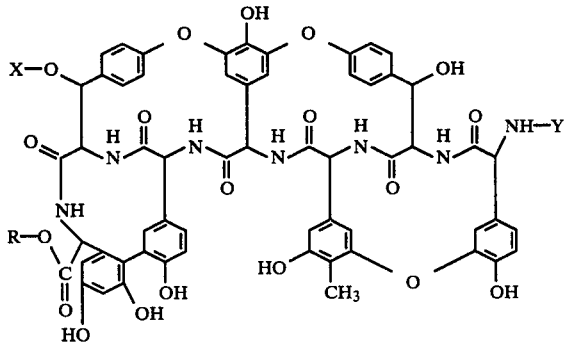

wherein R is hydrogen or loweralkyl, X is hydrogen or ristosamine, and Y is acyl and pharmaceutically acceptable salts thereof.

2. A method of treating bacterial infection in a patient suffering from an infection caused by a susceptible organism comprising administering to said patient a therapeutically effective amount of a compound of the formula

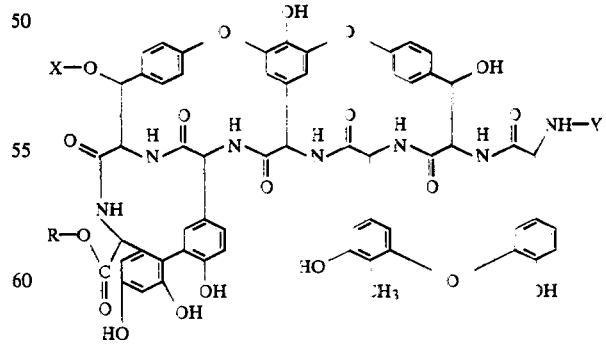

wherein R is hydrogen or loweralkyl, X is hydrogen or ristosamine, Y is acyl, or a pharmaceutically acceptable salt thereof.

3. The method of claim 2 wherein R and X are each hydrogen or a pharmaceutically acceptable salt thereof.

4. The method of claim 2 wherein R is hydrogen and X is ristosamine or a pharmaceutically acceptable salt thereof.

5. The method of claim 2 wherein R is methyl and X is ristosamine or a pharmaceutically acceptable salt thereof.

6. The method of claim 2 wherein R is methyl and X is hydrogen or a pharmaceutically acceptable salt thereof.

* * * * *